| United States Patent [19] | [11] | 4,151,173 |
| Vogel | [45] | Apr. 24, 1979 |

[54] ACYLATED POLYOXYALKYLENE POLYAMINES

[75] Inventor: Paul W. Vogel, Lyndhurst, Ohio

[73] Assignee: The Lubrizol Corporation, Wickliffe, Ohio

[21] Appl. No.: 364,217

[22] Filed: May 25, 1973

Related U.S. Application Data

[63] Continuation-in-part of Ser. No. 144,262, May 17, 1971, Pat. No. 3,806,456.

[51] Int. Cl.$^2$ .................. C07G 103/87; C08G 73/02; C07C 207/40
[52] U.S. Cl. .................. 260/326.5 F; 260/404.5; 260/561 N; 260/561 R
[58] Field of Search .................. 260/326.5 F, 561 N, 260/404.5, 561 R

[56] References Cited

U.S. PATENT DOCUMENTS

| 2,662,898 | 12/1953 | Ross et al. ......................... 260/326.5 |
| 3,272,746 | 9/1966 | LeSuer et al. ...................... 252/47.5 |
| 3,630,904 | 12/1971 | Musser et al. ................. 260/326.5 X |

*Primary Examiner*—Mark L. Berch
*Attorney, Agent, or Firm*—James W. Adams, Jr.; S. I. Khayat

[57] ABSTRACT

This invention is directed to oil-soluble acylated-nitrogen compositions having demulsifying characteristics obtained by reacting at least one carboxylic acid or carboxylic acid-producing compound having at least 8 aliphatic carbon atoms with an effective amount of at least one high molecular weight polyoxyalkylene polyamine; said polyamine having an average molecular weight of at least about 200. The acylated-nitrogen compositions of this invention are particularly useful as additives for a variety of oleaginous materials including, for example, lubricating oils, hydraulic fluids, lubricants, fuels, e.g., gasoline, diesel fuels, etc.

17 Claims, No Drawings

ACYLATED POLYOXYALKYLENE POLYAMINES

This application is a continuation-in-part of applicants copending application Ser. Number 144,262, filed May 17, 1971, now U.S. Patent 3,806,456.

This invention relates to oil soluble acylated-nitrogen compositions and more specifically to acylated-nitrogen compositions having demulsifying characteristics which are particularly useful as additives for a variety of oleaginous materials including lubricants, normally liquid fuels, e.g., gasoline, diesel fuels, etc., hydraulic fluids, lubricating oils and the like. More specifically, this invention is directed to acylated-nitrogen compositions and to a process for preparing said compositions which comprises (A) reacting at least one carboxylic acid or carboxylic acid-producing compound, e.g., an aliphatic, aromatic or aliphatic substituted aromatic acid or acid-producing compound having at least 8 aliphatic carbon atoms with (B) at least one high molecular weight polyoxyalkylene polyamine having an average molecular weight of at least about 200.

This invention relates more preferably to acylated-nitrogen compositions and to the process for preparing same which comprises reacting at least one substantially saturated, hydrocarbon-substituted carboxylic acid or acid-producing compound wherein said hydrocarbon substituent has at least about 8 aliphatic carbon atoms, e.g., an average molecular weight of at least about 100 with an effective amount of at least one high molecular weight polyoxyalkylene polyamine having an average molecular weight of at least about 200. The acylated-nitrogen compositions of this invention may be used either alone or in combination with other known additives, e.g., dispersants, extreme pressure agents, detergents, rust inhibitors, oxidation inhibitors, viscosity index improving agents, etc., in small but effective amounts in various oleaginous materials.

Presently, many nitrogen-containing compositions are being used as an additive in various lubricants or fuels, for example, in internal combustion engines, gears, power-transmitting units, etc. While these materials have achieved wide-spread acceptance there is still a need for additives which have improved demulsifying characteristics. More specifically, it is generally known that while these nitrogen-containing compositions are effective as additives for a variety of compositions including, for example, lubricating oils, fuels, etc., their presence however in some instances tends to promote emulsification in the presence of water. This is particularly true where, due to engine design, water vapor enters the crankcase and condenses on the internal surfaces thereof. This condition provides an ideal environment for the accumulation of water which may result in the formation of an emulsion.

Accordingly, to avoid these and other problems and to minimize or eliminate the formation of an emulsion, it has been found in accordance with this invention that acylated-nitrogen compositions having improved demulsifying characteristics can be obtained by reacting at least one carboxylic acid or carboxylic acid-producing compound having at least 8 aliphatic carbon atoms with an effective amount of one or more high molecular weight polyoxyalkylene polyamines. The acylated-nitrogen compositions particularly preferred for purposes of this invention may be obtained, for example, by reacting a substantially saturated, hydrocarbon-substituted carboxylic acid or carboxylic acid-producing compound with an effective amount, e.g., at least about 0.001 equivalent of at least one high molecular weight polyoxyalkylene polyamine. The acylated-nitrogen compositions of this invention when added to a lubricant or fuel, for example, have been found to eliminate or substantially reduce the formation of emulsions.

Therefore, it is an object of this invention to provide an acylated-nitrogen composition, having improved demulsifying characteristics, which may be used either alone or in combination with other known additives in oleaginous materials. It is another object of this invention to provide a high molecular weight oil soluble acylated-nitrogen composition and a process for preparing same; wherein said composition is particularly characterized by its demulsifying characteristics in the presence of other known additives.

These and other objects of the invention can be accomplished by providing an oil soluble, acylated-nitrogen composition having demulsifying characteristics prepared by reacting (A) at least one carboxylic acid or carboxylic acid-producing compound, e.g., an aliphatic, aromatic or aliphatic-substituted aromatic acid or acid-producing compound having at least 8 aliphatic carbon atoms with (B) at least about 0.001 equivalent of at least one high molecular weight polyoxyalkylene polyamine per equivalent of said acid or acid-producing compound. The polyoxyalkylene polyamines have average molecular weights of at least about 200 and preferably at least about 400.

Generally, for purposes of this invention, the acid or acid-producing compounds including the aliphatic, aromatic, or aliphatic-substituted aromatic acids or acid-producing compounds should have at least one and preferably at least two carboxylic acid or acid-producing groups. More specifically, the acids or acid-producing compounds include the monocarboxylic and polycarboxylic acids, e.g., di- and tri-carboxylic acids, etc., the anhydrides, halides, salts, e.g., ammonium salts, and lower alkyl esters derived from monohydric lower aliphatic alcohols, such as the methyl, ethyl, or propyl esters. The aliphatic or oil-solubilizing substituent of these carboxylic acids or acid-producing compounds should have at least about 8, preferably at least 16 and more preferably at least 50 aliphatic carbon atoms, e.g., an aliphatic or aliphatic-substituted aromatic carboxylic acid wherein the aliphatic substituent has at least about 8 aliphatic carbon atoms.

In a preferred embodiment, the acylated-nitrogen compositions of this invention may be prepared by utilizing a substantially hydrocarbon-substituted carboxylic acid or acid-producing compound, e.g., acrylic or maleic acid and the derivatives thereof, wherein said hydrocarbon substituent has at least about 8 and more preferably at least about 50 carbon atoms per carboxylic group, e.g., the aliphatic substituent has an average molecular weight of at least about 100. The requirement that the carboxylic acid or acid-producing compound have a lower limit of at least about 8 aliphatic carbon atoms is based not only upon the consideration of oil solubility of the acylated-nitrogen compositions but also upon the effectiveness of these compositions as additives for the purposes indicated, e.g., demulsifying agents, etc.

Moreover, it is preferred that the hydrocarbon substituent be substantially saturated, e.g., at least about 95% of the total number of carbon-to-carbon covalent linkages are substantially saturated linkages. Further, the substantially hydrocarbon substituent of the acylated-nitrogen composition, preferably, should be substantially free from oil solubilizing pendent groups, i.e., groups having more than about 6 aliphatic carbon atoms. While some oil solubilizing pendent groups may be present they should be present in an amount less than about one of said groups for about every 25 aliphatic carbon atoms in the main hydrocarbon chain.

In addition, the hydrocarbon substituent may contain a polar substituent provided that the polar substituent is not present in an amount sufficiently large to alter, significantly, the hydrocarbon character of the radical. Thus, the polar substituent may be present in an amount ranging up to about 20% by weight of the hydrocarbon substituent and preferably in an amount ranging up to about 10% by weight of the hydrocarbon substituent. The polar substituent may include, for example, chloro, bromo, keto, ethereal, aldehydo, nitro, etc. In the preferred embodiment, the substantially hydrocarbon substituent may comprise either a high molecular weight substantially-saturated petroleum fraction or a substantially-saturated olefin polymer, e.g., particularly a polymer of the mono-olfeins having from about 2 to 30 carbon atoms. For example, polymers which are particularly useful for this purpose include the polymers of 1-monoolefins, e.g., ethylene, propene, 1-butene, isobutene, 1-hexene, 1-octene, 2-methyl-1-heptene, 3-cyclohexyl-1-butene and 2-methyl-5-propyl-1-hexene. In addition, a polymer of an olefin wherein the olefinic linkage is not in the terminal position is likewise useful and may include, for example, 2-butene, 3-pentene, 4-octene, etc.

Also useful are the interpolymers of the olefins such as those illustrated above with other interpolymerizable olefinic materials, e.g., aromatic olefins, cyclic olefins, polyolefins, etc. These interpolymers, for example, may be prepared by polymerizing isobutene with styrene; isobutene with butadiene; propene with isoprene; ethylene with piperylene; isobutene with chloroprene; isobutene with p-methyl styrene; 1-hexene with 1,3-hexadiene; 1-octene with 1-hexene; 1-heptene with 1-pentene; 3-methyl-1-butene with 1-octene; 3,3-dimethyl-1-pentene with 1-hexene; isobutene with styrene and piperylene; etc. The relative proportions of the mono-olefins to the other monomers, in the interpolymers, influence the stability and oil solubility of the acylated-nitrogen compositions derived from these interpolymers. Thus, for reasons of oil solubility and stability the interpolymers contemplated in the preferred embodiment of this invention, should be substantially aliphatic and substantially saturated. In other words, the interpolymers should contain at least about 80% and preferably about 95% by weight of units derived from the aliphatic mono-olefins and no more than about 5% of olefinic linkages based on the total number of carbon-to-carbon covalent linkages. In the most preferred cases, the percent of the olefinic linkages should be less than about 2% of the total number of carbon-to-carbon covalent linkages.

Specific examples of these interpolymers include a copolymer of 95% by weight of isobutene with 5% of styrene; a terpolymer of 98% by weight of isobutene with 1% of piperylene and 1% of chloroprene; a terpolymer of 95% by weight of isobutene with 2% of 1-butene and 3% of 1-hexene; a terpolymer of 60% by weight of isobutene with 20% of 1-pentene and 20% of 1-octene; a copolymer of 80% by weight of 1-hexene and 20% of 1-heptene; a terpolymer of 90% by weight of isobutene with 2% of cyclohexene and 8% of propene; and a copolymer of 80% by weight of ethylene and 20% of propene. Another source of substantially hydrocarbon radicals comprises the saturated aliphatic hydrocarbons, e.g., highly refined high molecular weight white oils or the synthetic alkanes including those obtained by hydrogenating the high molecular weight olefin polymers illustrated hereinabove.

In the preferred embodiments, olefin polymers having average molecular weights ranging from about 400 to 10,000 and still more preferably ranging from about 700 to 5,000 may be used. The higher molecular weight olefin polymers, e.g., having average molecular weights ranging from about 10,000 to 100,000 or higher may be used, and they have been found to impart viscosity index improving properties to the acylated-nitrogen compositions. In many instances, however, the use of the higher molecular weight olefin polymers may be desirable.

Of the various acids or acid-producing compounds which may be used for purposes of this invention, the substantially-saturated, aliphatic-hydrocarbon substituted mono and dicarboxylic acids, e.g., acrylic or succinic acid and the derivatives thereof, are particularly preferred. For example, a high molecular weight succinic acid may be prepared by reacting maleic acid with a high molecular weight olefin, e.g., a chlorinated olefin polymer, at temperatures ranging from about 80° C. to about 250° C. until the desired product is obtained. If desired, any ethylenic unsaturation in the hydrocarbon substituent may be hydrogenated to saturated linkages. Either the anhydride or the acid may be converted to the corresponding halide or ester by reacting the acid or anhydride with various compounds including, for example, phosphorus halides, phenols, alcohols, etc. Another example for preparing a high molecular weight succinic acid or the anhydride thereof comprises the reaction of itaconic acid with either a high molecular weight olefin or a polar-substituted hydrocarbon at temperatures ranging from about 80° C. to about 250° C.

In addition to the dicarboxylic acids or acid-producing compounds, other polycarboxylic acids and the derivatives thereof having more than two carboxylic groups may be used for purposes of this invention. These polycarboxylic acids may be characterized as containing at least 8 aliphatic carbon atoms and preferably at least about 16 aliphatic carbon atoms and still more preferably at least about 50 aliphatic carbon atoms for each carboxylic group. Some of these acids may be obtained, for example, by halogenating a high molecular weight hydrocarbon, e.g., an olefin as described hereinabove to produce a polyhalogenated product which may be converted to a polynitrile and then subsequently hydrolyzed to the acid. Moreover, these acids may be prepared, for example, by the oxidation of a high molecular weight polyhydric alcohol with potassium permanganate, nitric acid or some other oxidizing agent. Still further, another example of a method for preparing a polycarboxylic acid comprises the reaction of an olefin or a polar-substituted hydrocarbon, e.g., chlorinated polyisobutene with an unsaturated polycarboxylic acid, e.g., 2-pentene-1,3,5-tricarboxylic acid obtained by the dehydration of citric acid.

Still further, other polycarboxylic acid or acid-producing compounds which may be used for purposes of this invention include the tricarboxylic acids and the derivatives thereof, e.g., the esters. These polycarboxylic acids or their esters may be converted to high molecular weight compositions by reacting the acids or esters, etc. with a high molecular weight hydrocarbon, e.g., an olefin polymer or a polar-substituted hydrocarbon, i.e., a halogenated polyisobutene, etc. A method for converting these acids or acid-producing compounds, e.g., acrylic acid, maleic acid or a tricarboxylic acid, etc. to high molecular weight acids or acid-producing compounds are well known and may be found, for example, in U.S. Pat. Nos. 3,219,666 and 3,454,607. As indicated, the aliphatic portion or substituent of the acid or the derivatives thereof may have an average molecular weight ranging from about 100 to 10,000 or higher and preferably from about 700 to 5,000.

For purposes of this invention, a particular class of tricarboxylic acid esters, for example, may be obtained by reacting an acrylic compound, e.g., methyl acrylate, with a maleic-acid ester or a fumaric-acid ester in the presence of a catalytic amount of an organic tertiary phosphorus compound selected from the group consisting of tertiary phosphines and tertiary phosphoramides. More specifically, these tricarboxylic-acid esters may be prepared by reacting the maleic-acid ester or the fumaric-acid ester, for example, in amounts ranging from about 0.1 to 5.0 mole equivalents and preferably from about 0.3 to 1.5 mole equivalents per equivalent of the acrylic compound in the presence of the catalyst. The catalyst should be present in catalytic amounts, e.g., 0.0001 to 0.1 mole equivalents of the organic tertiary phosphorus compound per equivalent of said acrylic compound. These tricarboxylic-acid esters may be converted to their corresponding acids by hydrolysis of said esters in a known manner. Specific examples of the various tricarboxylic-acid esters which may be converted to high molecular weight acid-producing compounds for purposes of this invention include 1,2,3-trimethoxycarbonyl butane-3; 1,2,3-triethoxycarbonyl butene-3; 1,2,3-tri-n-butoxycarbonyl butene-3; 1,2-dimethoxycarbonyl-3-ethoxycarbonyl butene-3; 1,2-diethoxycarbonyl-3-methoxycarbonyl butene-3; 1,2-dicyclohexyloxycarbonyl-3-methoxycarbonyl butene-3; 1,3-dimethoxycarbonyl-2-ethoxycarbonyl butene-3; 1,2-dicyclohexyloxycarbonyl-3-ethoxycarbonyl butene-3; 1,2,3-triallyloxycarbonyl butene-3; 1,2-diallyloxycarbonyl-3-methoxycarbonyl butene-3; 1,2-diallyloxycarbonyl-3-ethoxycarbonyl butene-3; 1,2-di-n-butoxycarbonyl-3-methoxycarbonyl butene-3; 1,2-di-n-butoxycarbonyl-3-ethoxycarbonyl butene-3; 1,2-di-ethoxycarbonyl-3-n-propoxycarbonyl butene-3; 1,2-di-octyloxycarbonyl-3-methoxycarbonyl butene-3; 1,2-di-ethoxycarbonyl-3-(2-hydroxyethoxy)carbonyl butene-3; 1,2-dimethoxycarbonyl-3-phenoxycarbonyl butene-3; 1,2-diphenoxycarbonyl-3-methoxycarbonyl butene-3; 1,2-dimethoxycarbonyl-3-stearyloxycarbonyl butene-3, etc.

Other acids include the monocarboxylic acids and the derivatives thereof which have at least 8 and preferably at least 16 aliphatic carbon atoms. The monocarboxylic acids or acid-producing compounds which may be used for purposes of this invention may be obtained, for example, by oxidizing a monohydric alcohol with potassium permanganate or by reacting a halogenated high molecular weight olefin polymer with a ketene. Another method for preparing a monocarboxylic acid or acid-producing compound comprises reacting metallic sodium with an acetoacetic ester or a malonic ester of an alkanol to form the sodium derivative of the ester and then subsequently reacting the sodium derivative with a halogenated high molecular weight hydrocarbon, e.g., brominated wax or brominated polyisobutene.

Other acids having at least 8 aliphatic carbon atoms which may be used include, for example, capric, undecylic, lauric acid, tridecoic acid, myristic acid, pentadecanoic acid, palmitic acid, stearic acid, non-decylic acid, arachidic acid, behenic acid, hyenic acid, cerotic acid, montanic acid, linoleic acid, linolinic acid, etc.

Other carboxylic acids or acid-producing compounds which may be used include the aromatic acids or the substituted aromatic acids having one or more carboxylic acids or acid-producing groups, e.g., ester groups, and at least one aliphatic hydrocarbon chain or substituent with 8 or more aliphatic carbon atoms. These acids may include, for example, p-isobutylhydratropic acid (Ibuprofen), o-pentadecadieneyl salicylic acid (Anacardic acid), 4-para[bis(2-chloroethyl)amino]phenyl butaric acid (Chlorambucyl) and Indopol salicylic acid and the salts thereof.

The polyamines which may be used for purposes of this invention comprise the polyoxyalkylene polyamines, e.g., diamines and triamines which have average molecular weights ranging from about 200 to 4000 and preferably from about 400 to 2000. Illustrative examples of these polyoxyalkylene polyamines may be characterized by the following formulae.

Formula I

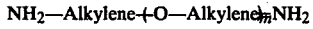

where m has a value of about 3 to about 70 and preferably about 10 to about 35.

Formula II

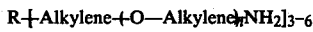

where n is such that the total value of n is from about 1 to about 40 with the proviso that the sum of all the n's is from about 3 to about 70 and usually from about 6 to about 35. R is a polyvalent saturated hydrocarbon radical of up to ten carbon atoms having a valence of 3-6, as appropriate. The alkylene groups may be straight or branched chains and will contain from 1 to 7 carbon atoms, usually 1 to 4 carbon atoms. The various alkylene groups present within Formulae I and II may be the same or different. Examples of these alkylene groups include:

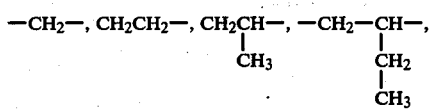

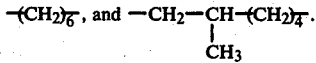

More specific examples of polyamines within Formulae I and II include:

Formula III

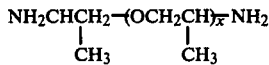

wherein x has a value of from about 3 to 70 and preferably from about 10 to 35 and by the formula:

Formula IV

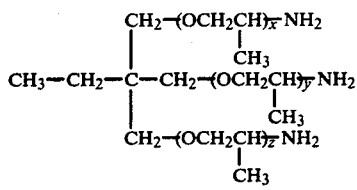

wherein x+y+z have a total value ranging from about 3 to 30 and preferably from about 5 to 10.

The preferred polyoxyalkylene polyamines for purposes of this invention include the polyoxyethylene and polyoxypropylene diamines and the polyoxypropylene triamines having average molecular weights ranging from about 200 to 2000. The polyoxyalkylene polyamines are commercially available and may be obtained, for example, from the Jefferson Chemical Company, Inc. under the trade name "Jeffamines D-230, D-400, D-1000, D-2000, T-403, etc."

A convenient process for preparing the acylated-nitrogen composition of this invention comprises reacting at least about 0.001 equivalent of a high molecular weight polyoxyalkylene polyamine characterized by having within its structure at least two radicals with the structural configuration

with approximately one equivalent of a high molecular weight carboxylic acid or carboxylic acid-producing compound having within its structure an oil-solubilizing group comprising at least 8 aliphatic carbon atoms. The carboxylic acid or carboxylic acid-producing compounds may be characterized further as having at least one acid or acid-producing group characterized by the formula:

wherein X selected from the class consisting of halogen, hydroxy, hydrocarbonoxy, and acyloxy radicals.

The reaction between the polyamine and the carboxylic acid or acid-producing compound results in the direct attachment of the nitrogen atoms to the polar radical, i.e., acyl, acylimidoyl or acyloxy radical derived from the acid or acid-producing group. The linkage formed between the nitrogen atom and said polar radical may be characterized as an amide, imide, amidine, salt or a mixture of these radicals. The precise relative proportions of these radicals in a particular product, generally, is not known since it depends to a large extent upon the type of acid or acid-producing group and the conditions, e.g., temperatures, etc., under which the reaction is carried out. For example, a reaction involving an acid or an acid anhydride with a polyamine at temperatures below about 50° C. will result predominantly in a salt linkage. However, at relatively higher temperatures, e.g., above about 80° C. up to about 250° C., the result obtained is predominantly an imide, amide or amidine linkage or a mixture thereof. In any event, the products obtained by the process irrespective of the relative proportions of the linkages present in the reaction product have been found to be effective for purposes of this invention.

In preparing the acylated-nitrogen compositions of this invention, the process comprises heating a mixture of the acid or acid-producing compound and the polyamine, e.g., one or more polyoxyalkylene polyamines at temperatures ranging from about room temperatures, e.g., 25° C. up to about the decomposition temperature of the reactants or the products being prepared. Preferably, the reaction temperatures used in preparing the acylated-nitrogen compositions range from about 50° C. up to about 300° C. and more preferably from about 80° C. to about 250° C. When the acid or the anhydride thereof is employed, the reaction with the nitrogen-containing compound, e.g., polyoxyalkylene polyamine may be carried out at lower temperatures, e.g., temperatures ranging from about 80° C. to about 125° C. to obtain products having predominantly salt linkages or a mixture of salt and amide linkages. The acylated products obtained at these lower reaction temperatures may be converted, if desired, by heating them to temperatures above about 80° C., e.g., from about 125° C. to about 250° C. to obtain products having predominantly amide, imide, or amidine linkages. The reaction, if desirable, may be carried out in various solvents which must be substantially inert with respect to the reactants and may include, for example, benzene, toluene, naphtha, xylene, mineral oil, hexane, and various combinations of these inert diluents.

The relative proportions of the acid or acid-producing compound and the polyoxyalkylene polyamine to be used in the process are such that at least about 0.001 stoichiometric equivalent of the polyamine is used for each equivalent of the acid or acid-producing compound. More preferably, the polyoxyalkylene polyamine may be present in an amount ranging from about 0.001 to 4.0 equivalents and still more preferably from about 0.1 to 2.0 equivalents for each equivalent of the acid or acid-producing compound. In many instances, however, the polyoxyalkylene polyamine will be present in the reaction in the amount of approximately 1.0 equivalent of said polyamine for each equivalent of said acid or acid-producing compound. For purposes of this invention it should be understood that the equivalent weight of the nitrogen containing compound, i.e., polyoxyalkylene polyamine, is based on the number of nitrogen containing radicals, i.e., amino groups, defined by the structural configuration

Thus, for example, the equivalent weight of a polyoxyalkylene diamine having two amino groups would be the molecular weight of the diamine divided by 2. Similarly, the equivalent weight of the acid or acid-producing compound is calculated on the number of acid or acid-producing radicals defined by the structural configuration

wherein X is either a halogen, hydroxy, hydrocarbonoxy or acyloxy radical.

The following examples illustrate the products and the process for preparing the acylated-nitrogen compositions of this invention.

EXAMPLE 1

A polyisobutenyl succinic anhydride is prepared by reacting chlorinated polyisobutylene with maleic anhydride at a temperature of about 200° C. The polyisobutenyl radical has an average molecular weight of about 850 and the resulting hydrocarbon substituted anhydride is found to have an acid number of about 113 which corresponds to an equivalent weight of about 500. Approximately 3,270 parts by weight (6.0 equivalents) of the polyisobutenyl succinic anhydride is added to a 5-liter flask fitted with a stirrer, thermowell, nitrogen inlet tube, and a Dean-Stark trap at about room temperature. The polyisobutenyl succinic anhydride is heated to about 150° C. and approximately 600 parts by weight (3.0 equivalents) of a polyoxypropylene diamine having a molecular weight of about 400 is added to the flask through an addition funnel. The polyoxypropylene diamine is added to the reaction over a period of about 1¼ hours. The reactants are held at a temperature of about 150° C. for about 3 hours while blowing with nitrogen. The reaction product is subsequently filtered with about 3% of a filter aid at 150° C. The filtered product is analyzed and found to have a nitrogen content of 1.12%.

EXAMPLE 2

A polyisobutenyl succinic anhydride is prepared by reacting chlorinated isobutylene with maleic anhydride at a temperature of about 200° C. The polyisobutenyl radical has an average molecular weight of about 850 and the resulting hydrocarbon substituted anhydride is found to have an acid number of 113 which corresponds to an equivalent weight of about 500. Approximately 3,270 parts by weight (6.0 equivalents) of the polyisobutenyl succinic anhydride is added to a 5-liter flask fitted with a stirrer, thermowell, Dean-Stark trap and a subsurface inlet tube at room temperature. The reactant is heated to a temperature of about 150° C. at which time approximately 354 parts by weight (3.0 equivalents) of a polyoxypropylene diamine having a molecular weight of about 230 is added to the reaction through an addition funnel while blowing with nitrogen over a period of about 1½ hours. The reactants are held at a temperature of about 150°-155° C. for a period of about 3 hours while blowing with nitrogen. Approximately 40 parts by weight of water are collected from the reactor. The reaction is heated to a temperature of about 150° C. and filtered with about 3% by weight of a filter aid. The filtered product is analyzed and found to have a nitrogen content of about 1.12%.

EXAMPLE 3

A polyisobutenyl succinic anhydride is prepared by reacting a chlorinated polyisobutylene with maleic acid anhydride at a temperature of about 200° C. The polyisobutenyl radical has an average molecular weight of about 850 and the resulting hydrocarbon substituted anhydride is found to have an acid number of about 113 which corresponds to an equivalent weight of about 500. Approximately 2,726 parts by weight (5 equivalents) of the polyisobutenyl succinic anhydride is added to a 5-liter, four-necked flask at room temperature; said flask is fitted with a stirrer, thermowell, Dean-Stark trap and a subsurface inlet tube. The reactants are heated to a temperature of about 90° C. and approximately 769 parts by weight of mineral oil are added to the flask and subsequently heated to a temperature of about 150° C. Subsequently, about 388 parts by weight (2.5 equivalents) of a polyoxypropylene triamine having a molecular weight of about 400 is added to the flask through an addition funnel while blowing with nitrogen over a period of about 2 hours at a temperature of about 150° C. The reaction is held for a period of about 3 hours while blowing with nitrogen at temperatures ranging from about 150°-153° C. Approximately 29 parts by weight of water is collected. While at a temperature of about 150° C., approximately 3% of a filter aid is added and the product is filtered. The filtered product is analyzed and found to have a nitrogen content of about 0.89%.

EXAMPLE 4

A polyisobutenyl succinic anhydride is prepared by reacting a chlorinated polyisobutylene with maleic anhydride at a temperature of about 200° C. The polyisobutenyl radical has an average molecular weight of about 850 and the resulting hydrocarbon substituted anhydride is found to have an acid number of approximately 113 which corresponds to an equivalent weight of about 500. Approximately 1,320 parts by weight of the polyisobutenyl succinic anhydride (1.2 equivalents) is added to a 3-liter flask and heated to a temperature of about 120° C. over a period of about ¾ hour while blowing with nitrogen. At a temperature of approximately 120° C., about 321 parts by weight (0.6 equivalent) of a polyoxypropylene diamine having a molecular weight of about 1000 is added to the flask over a period of about ½ hour while blowing with nitrogen. The reaction mixture is heated to a temperature of about 150° C. and held at temperatures of about 150°-155° C. for approximately 1 hour while blowing with nitrogen. At a temperature of about 150° C., approximately 3% by weight of a filter aid is added to the mixture and the product is filtered. The filtered product is analyzed and found to have a nitrogen content of approximately 0.52%.

EXAMPLE 5

A polyisobutenyl succinic anhydride is prepared by reacting a chlorinated polyisobutylene with maleic anhydride at a temperature of about 200° C. The polyisobutenyl radical has an average molecular weight of about 850 and the resulting hydrocarbon substituted anhydride is found to have an acid number of approximately 113 which corresponds to an equivalent weight of about 500. The reaction product, comprising the polyisobutenyl succinic anhydride, is extracted with methyl alcohol to remove any of the lower molecular weight fractions. The resulting polyisobutenyl succinic anhydride has a saponification number of about 250. Approximately 224 parts by weight of the alcohol treated polyisobutenyl succinic anhydride (1.0 equivalent) is added to a flask at about room temperature and then heated to about 125° C. over a period of about ¾ hour while blowing with nitrogen. Approximately 268 parts by weight (0.5 equivalent) of a polyoxypropylene diamine having a molecular weight of about 1000 is added to the reaction at a temperature of about 125° C. over a period of ½ hour while blowing with nitrogen. The reaction mixture is heated to 150° C. over a period of about ¼ hour and held at a temperature of about 150°-155° C. for about 1 hour while blowing with nitrogen. At a temperature of about 150° C., approximately 3% by weight of a filter aid is added to the reaction mixture and the product is filtered. The filtered product is analyzed and found to have a nitrogen content of about 1.43%.

EXAMPLE 6

A polyisobutenyl succinic anhydride is prepared by reacting a chlorinated polyisobutylene with maleic anhydride at 200° C. The polyisobutenyl radical has an average molecular weight of about 850 and the resulting hydrocarbon substituted anhydride is found to have an acid number of approximately 113 which corresponds to an equivalent weight of about 500. Approximately 2,720 parts by weight (5.0 equivalents) of the polyisobutenyl succinic anhydride is added to a 5-liter flask fitted with a stirrer, thermowell, a nitrogen inlet tube and a Dean-Stark trap. Approximately 1,339 parts by weight (2.5 equivalents) of a polyoxypropylene diamine having a molecular weight of about 1000 is added to the reaction at a temperature of about 150° C. and held at this temperature for about 6 hours. Approximately 27 parts by weight of water is collected. At a temperature of about 150° C., approximately 3% by weight of a filter aid is added to the reaction mixture and the product is filtered. The filtered product is found to have a nitrogen content of about 0.91%.

EXAMPLE 7

A polyisobutenyl succinic anhydride is prepared by chlorinating a polyisobutene having an average molecular weight of about 1800 while simultaneously reacting same with a stoichiometric amount of maleic anhydride at a temperature of about 200° C. in the presence of phenothiazine. Approximately 1,550 parts by weight (2 equivalents) of the chlorinated polyisobutenyl succinic anhydride is added to a 5-liter, four-necked flask with approximately 1,380 parts by weight of mineral oil. The flask is fitted with a stirrer, thermowell, nitrogen inlet tube and a Dean-Stark trap. The reactant is heated to a temperature of about 80° C. while blowing with nitrogen and approximately 535 parts by weight (1.0 equivalent) of a polyoxypropylene diamine having a molecular weight of about 1000 is added to the reaction over a period of about ½ hour at a temperature ranging from 80°-100° C. The reaction mixture is heated to a temperature of approximately 150° C. and held at 150°-155° C. for about 5 hours while blowing with nitrogen. Approximately 12 parts by weight of water is collected. About 3% by weight of a filter aid is added to the reaction mixture and the product is filtered at a temperature of about 150° C. The filtered product obtained is analyzed and found to have a nitrogen content of about 0.41%.

EXAMPLE 8

A polyisobutenyl succinic anhydride is prepared by reacting a chlorinated polyisobutylene with maleic anhydride at a temperature of about 200° C. The polyisobutenyl radical has an average molecular weight of about 850 and the resulting hydrocarbon substituted anhydride is found to have a saponification number of 101 which corresponds to an equivalent weight of about 555. Approximately 111 parts by weight (0.2 equivalent) of the polyisobutenyl succinic anhydride is mixed with approximately 53 parts by weight (about 0.1 equivalent) of a polyoxypropylene diamine at room temperature. The reaction mixture is heated to a temperature of about 150° C. over a period of about ½ hour while blowing with nitrogen. The reaction mixture is held at a temperature of about 150°-161° C. for about an hour while blowing with nitrogen. Approximately 2 parts by weight of water is collected. The reaction mixture is cooled to about room temperature under nitrogen and then filtered. The filtered product is analyzed and the nitrogen content is approximately 1.03%.

EXAMPLE 9

A polyisobutenyl succinic anhydride is prepared by reacting a chlorinated polyisobutylene with maleic anhydride at about 200° C. The polyisobutenyl radical has an average molecular weight of about 850 and the resulting hydrocarbon substituted anhydride is extracted with methyl alcohol to obtain a product having a saponification number of about 250. Approximately 51 parts by weight (0.228 equivalent) of the polyisobutenyl succinic anhydride, treated with the methyl alcohol, is reacted with approximately 60 parts by weight (0.114 equivalent) of a polyoxypropylene diamine. The reaction mixture is heated to a temperature of about 149° C. over a period of ½ hour while blowing with nitrogen. The reaction is continued for about 1 hour at a temperature of about 149°-156° C. while blowing with nitrogen and collecting approximately 2 parts by weight of water. The reaction mixture is cooled to room temperature under nitrogen, filtered and analyzed. The filtered product is found to have a nitrogen content of 1.69%.

EXAMPLE 10

A polyisobutenyl succinic anhydride is prepared by reacting a chlorinated polyisobutylene with maleic anhydride at 200° C. The polyisobutenyl radical has an average molecular weight of about 850 and the resulting hydrocarbon substituted anhydride is found to have a saponification number of about 250 after being extracted with methyl alcohol. Approximately 25 parts by weight (0.11 equivalent) of the alcohol extracted polyisobutenyl succinic anhydride is mixed with approximately 58 parts by weight (0.055 equivalent) of a polyoxypropylene diamine having a molecular weight of about 2000 at room temperature. The reaction mixture is subsequently heated to approximately 150° C. over a period of ½ hour while blowing with nitrogen. The reaction mixture is then held at a temperature of about 151°-157° C. for an hour while blowing with nitrogen. Water is collected from the reaction and the reaction product is filtered and cooled to room temperature. The filtered product is analyzed and the nitrogen content is approximately 0.93%.

EXAMPLE 11

A polyisobutenyl succinic anhydride is prepared by the reaction of a chlorinated polyisobutylene with maleic anhydride at 200° C. The polyisobutenyl radical has an average molecular weight of about 850 and the resulting hydrocarbon substituted anhydride is found to have an acid number of about 113 which corresponds to an equivalent weight of about 500. Approximately 58 parts by weight (0.11 equivalent) of the polyisobutenyl succinic anhydride is mixed with approximately 58 parts by weight (0.055 equivalent) of a polyoxypropylene diamine at room temperature. The reaction mixture is heated to about 150° C. over a period of about ½ hour and held at a temperature of about 149°-153° C. for an hour while blowing with nitrogen. The reaction product is cooled to room temperature under nitrogen, filtered and analyzed. The filtered product is found to have a nitrogen content of 0.6%.

EXAMPLE 12

A polyisobutenyl succinic anhydride is prepared by the simultaneous chlorination of polyisobutylene and the reaction of said polyisobutylene with maleic anhydride at a temperature of about 200° C. The polyisobutenyl radical has an average molecular weight of 1500. Approximately 121 parts by weight (0.11 equivalent) of the polyisobutenyl succinic anhydride is mixed at room temperature with 58 parts by weight (0.055 equivalent) of a polyoxypropylene diamine and heated to a temperature of about 148° C. over a period of about ½ hour while blowing with nitrogen. The reaction mixture is held at a temperature of about 148°–154° C. for about an hour while blowing with nitrogen. The reaction product was cooled to about room temperature under nitrogen, filtered and analyzed. The filtered product is found to have a nitrogen content of 0.45%.

EXAMPLE 13

A polyisobutenyl succinic anhydride is prepared by simultaneously chlorinating a high molecular weight polyisobutylene having an average molecular weight of about 115,000 while reacting same with maleic anhydride at a temperature of about 200° C. Approximately 579 parts by weight (0.06 equivalent) of the polyisobutylene succinic anhydride is mixed at room temperature with approximately 30 parts by weight (0.03 equivalent) of a polyoxypropylene diamine and then heated to a temperature of about 200° C. over a period of about ½ hour while blowing with nitrogen. The reaction mixture is held at the temperature of about 205° C. for ¾ hour while blowing with nitrogen and then cooled to a temperature of about 107° C. At this temperature, an additional amount of mineral oil is added to the reaction product to obtain a total mineral oil content of about 78.2% and the temperature is maintained at about 100°–170° C. Approximately 5% of a filter aid is added to the reaction product and the product is filtered at a temperature of about 50°–70° C. The filtered product is analyzed and the nitrogen content is 0.03%.

EXAMPLE 14

A polyisobutenyl substituted succinic acid is prepared by the hydrolysis of the corresponding anhydrides (prepared by the condensation of a chlorinated polyisobutylene and maleic anhydride). To approximately 1.5 equivalents of a 70% mineral oil solution of the polyisobutenyl succinic acid having an acid number of 62 is added approximately 1.0 equivalent of a polyoxyalkylene triamine having an average molecular weight of about 1000. This mixture is heated to a temperature of 150°–167° C. for about 7 hours during which time water is removed from the reaction. The reaction product is diluted with approximately 174 parts by weight of mineral oil and then filtered at about 150° C.

EXAMPLE 15

A methyl ester of a high molecular weight mono-carboxylic acid is prepared by heating an equi-molar mixture of a chlorinated polyisobutene having a molecular weight of about 1000 and a chlorine content of 4.7% by weight with methyl methacrylate at 140°–220° C. The resulting ester is reacted with a stoichiometric equivalent of a polyoxyethylene diamine having an average molecular weight of about 1000 at 100°–200° C. to obtain an acylated-nitrogen product.

EXAMPLE 16

A mixture of about 2000 parts by weight of mineral oil, about 3.0 equivalents of a polyoxyethylene triamine having an average molecular weight of about 1000 and about 3.0 equivalents of a high molecular weight tricarboxylic acid is heated to about 150° C. and reacted for about 20 hours. The tricarboxylic acid is prepared by reacting a brominated poly(1-hexene) having a molecular weight of about 2000 and a bromine content of about 4% by weight with 2-pentene-1,3,5-tricarboxylic acid (prepared by dehydration of citric acid). The acylated-nitrogen product is filtered and a homogeneous mineral oil solution of the product is obtained.

EXAMPLE 17

To a solution of about 1.0 equivalent of the dimethyl ester of a polyethylene (molecular weight of about 1500)-substituted malonic acid in 5000 parts by weight of xylene, is added about 1.0 equivalent of a polyoxyethylene diamine having an average molecular weight of about 2000 at a temperature of about 60° C. The mixture is heated to the reflux temperature and held there for about 25 hours. The reaction product is then mixed with about 2000 parts by weight of mineral oil and the xylene is removed by heating the oil solution to a temperature of about 180° C.

EXAMPLE 18

A high molecular weight monocarboxylic acid is prepared by heating a chlorinated polyisobutene having a molecular weight of 350 and a chlorine content of 11.7% (7,000 parts by weight) with acrylic acid (1,440 parts by weight) at 80°–120° C. while hydrogen chloride is evolved from the reaction mixture. The reaction mixture is then heated to about 210° C. and filtered. The product has a chlorine content of 0.35% and an acid number of 114. About 7.0 equivalents of the high molecular weight monocarboxylic acid and about 7.0 equivalents of a polyoxyethylene diamine having an average molecular weight of about 1000 is mixed with about 2500 parts by weight of mineral oil and heated to about 200° C. The reaction product is filtered and a mineral oil solution of the acylated polyamine is obtained.

EXAMPLE 19

A chlorinated polyisobutene having a molecular weight of about 1000 and a chlorine content of 4.5% (6300 parts by weight, 8 equivalents of chlorine) is mixed with acrylic acid (940 parts by weight, 13 equivalents) and the mixture is heated to 230° C. while hydrogen chloride is evolved. The product is heated to 130°–182° C. and filtered. The product has an acid number of 63 and a chlorine content of 0.62%. Approximately 3,430 parts by weight (4 equivalents) of the monocarboxylic acid with about 4 equivalents of a polyoxyethylene diamine having a molecular weight of about 1000 and about 2,377 parts by weight of mineral oil are heated to 160°–200° C. for about 5 hours while water is being distilled off. The reaction mixture is heated at 200°–245° C. and subsequently filtered. A mineral oil solution of the acylated polyamine is obtained.

EXAMPLE 20

A mixture of ethyl acrylate (1 equivalent) and a chlorinated polyethylene having a molecular weight of 1500 and a chlorine content of 0.5% (1 equivalent of chlorine) is heated at 150°–250° C. for 15 hours. The reaction mixture is then heated at 200° C. and filtered. A mixture of 2 equivalents of polyoxyethylene diamine having an average molecular weight of about 1000 and approximately 1 equivalent of the above acid-producing composition is diluted with an equal amount of xylene and heated at reflux temperature until no water is distilled off. The reaction mixture is blended with an equal amount of mineral oil and heated to about 150°–170° C. The reaction product is then filtered.

EXAMPLE 21

A chlorinated polyisobutene having a molecular weight of 1000 and a chlorine content of 4.3% (6,550 parts by weight, 8 equivalents) and propyl alpha-chloroacrylate (720 parts by weight, 10 equivalents) are heated at 170°–220° C. for 17 hours and then at 180° C. The reaction product is filtered. A mixture of about 2 equivalents of a polyoxyethylene diamine having an average molecular weight of about 1000 and 1.5 equivalents of the above acid-producing composition is diluted with an equal amount of xylene and the resulting mixture is heated at reflux temperature until no water distilled off. The resulting product is a xylene solution of the acylated amine.

EXAMPLE 22

Tricyclohexyl phosphine (0.75 parts by weight) is added to a solution of 8.5 parts by weight of methyl acrylate and 15.5 parts by weight of diethyl fumarate in 45 parts by weight of dioxane in a stream of nitrogen and the mixture is heated to 100° C. for 10 hours. After the addition of 0.5 parts by weight of p-toluene sulfonic acid, the solvent is removed by distillation from the reaction product along with the elmination of any unreacted substance, followed by distillation in a high vacuum distillation apparatus. The product is 3-butene-1,2,3-tricarboxylic acid (1,2-diethyl, 3-methyl) ester having a boiling point of 101° C. at $3 \times 10^{-3}$ mm.Hg. The ester of the tricarboxylic acid is converted to a high molecular weight carboxylic acid-producing composition by reacting same with a chlorinated polyisobutene having a molecular weight of about 350 and a chlorine content of 11.7% at a temperature ranging from about 80°–120° C. A mixture of about 2000 parts by weight of mineral oil, 6.0 equivalents of a polyoxyethylene diamine having an average molecular weight of about 1000 and 3.0 equivalents of the above-mentioned high molecular weight tricarboxylic acid-producing composition is heated at 150°–200° C. for about 20 hours. The reaction product is filtered to obtain a homogeneous mineral oil solution of the acylated polyamine.

EXAMPLE 23

Tricyclohexyl phosphine (0.3 parts by weight) is added to a solution of 5 parts by weight of ethyl acrylate and 8 parts by weight of diethyl fumarate in 30 parts by weight of dioxane in a nitrogen stream, and the mixture is heated for 15 hours in a water vapour bath. After recovery of the unreacted substance, the reaction product mixture is distilled by a high vacuum distillation apparatus. The product obtained is 3-butene-1,2,3-tricarboxylic acid triethyl ester. The ester of the tricarboxylic acid is converted to a high molecular weight carboxylic acid-producing composition by reacting same with a chlorinated polyisobutene having a molecular weight of about 1000 and a chlorine content of about 4.5% at a temperature ranging from about 80°–120° C. A mixture of about 2000 parts by weight of mineral oil, 3.0 equivalents of a polyoxyethylene triamine having an average molecular weight of about 2000 and about 3.0 equivalents of the above-mentioned high molecular weight tricarboxylic acid-producing composition is heated to about 150°–200° C. for about 20 hours. The resulting reaction product is filtered and a homogeneous mineral oil solution of the acylated polyamine is obtained.

EXAMPLE 24

To a boiling solution of 0.9 parts by weight of tricyclohexyl phosphine in 150 parts by weight of peroxide-free dioxane is added a mixture of 80 parts by weight of methyl acrylate and 115 parts by weight of dimethyl maleate in 300 parts by weight of purified dioxane during a period of 3 hours in an atmosphere of nitrogen. After the addition, the mixture is heated further for 2 hours. Then a solution of 0.5 parts by weight of p-toluene sulfonic acid in 10 parts by weight of dioxane is added to the reaction mixture. After recovery of the unreacted substance, the reaction product mixture is distilled. The product obtained is (96% yield based on the reacted dimethylmaleate) 3-butene-1,2,3-tricarboxylic acid trimethyl ester. The ester of the tricarboxylic acid is converted to a high molecular weight carboxylic acid-producing composition by reacting same with a chlorinated polyisobutene having a molecular weight of about 350 and a chlorine content of 11.7% at a temperature ranging from about 80°–120° C. A mixture comprising approximately 2000 parts by weight of mineral oil, 3.0 equivalents of a polyoxyethylene triamine having an average molecular weight of 1000 and approximately 3.0 equivalents of the above-mentioned high molecular weight tricarboxylic acid-producing composition is heated to a temperature of about 150°–200° C. for about 20 hours. The reaction product is filtered and a homogeneous mineral oil solution of the acylated polyamine is obtained.

EXAMPLE 25

A mixture of 4.3 parts by weight of methyl acrylate, 7.7 parts by weight of diethyl fumarate and 0.5 parts by weight of diphenyl(4-oxy-butyl)phosphine is boiled and refluxed for 10 hours in a nitrogen stream. Distillation of the reaction product mixture gave a 3-butene-1,2,3-tricarboxylic acid (1,2-diethyl, 3-methyl) ester. The ester of the tricarboxylic acid is converted to a high molecular weight carboxylic acid-producing composition by reacting same with a chlorinated polyisobutene having a molecular weight of about 1000 and a chlorine content of about 4.5% at a temperature ranging from about 80°–120° C. A mixture of approximately 2000 parts by weight of mineral oil, 3.0 equivalents of a polyoxyethylene triamine having an average molecular weight of about 1000 and approximately 3.0 equivalents of the above-mentioned high molecular weight tricarboxylic acid-producing composition is heated to temperatures of 150°–200° C. over a period of 15 to 20 hours. The resulting product is filtered to give a homogeneous mineral oil solution of the acylated polyamine.

EXAMPLE 26

Approximately 4 equivalents of para-isobutylhydratropic acid and about 4 equivalents of polyoxypropylene diamine having an average molecular weight of about 1000 together with about 2000 parts by weight of mineral oil are heated to temperatures of about 85°–100° C. over a period of about 5 hours. Subsequently, the reaction mixture is heated to temperatures ranging up to about 200° C. and filtered. A mineral oil solution of the acylated polyamine is obtained.

EXAMPLE 27

Approximately 2 equivalents of stearic acid and about 2 equivalents of a polyoxypropylene diamine having an average molecular weight of about 1000 together with about 2000 parts by weight of mineral oil are heated at temperatures ranging up to about 125° C. over a period of about 4 hours. Subsequently, the reaction mixture is heated to temperatures ranging up to about 200° C. and filtered. A mineral oil solution of the acylated polyamine is obtained.

The oil soluble acylated-nitrogen compositions of this invention, which have improved demulsifying characteristics may be used as an additive for a variety of oleaginous materials, including, for example, synthetic and mineral lubricating oils, normally liquid fuels, e.g., gasoline, etc., in amounts ranging from about 0.001 to 20% by weight and preferably in amounts ranging from about 0.1 to 15% or 0.1 to 10% by weight of the total composition. Optimum amounts, however, will depend upon the particular type of surface or conditions to which the fuel or lubricant is to be subjected. Thus, for example, if the additive is to be used in gasoline for an internal combustion engine an amount ranging from about 0.001 to 1.0% by weight of the acylated-nitrogen composition may be sufficient; whereas, if said additive is to be used in a gear lube or in a diesel engine the amount of additive may range as high as 20% of the total weight. In some instances, however, even larger percentages, e.g., up to about 25% by weight of the additive may be utilized depending upon the particular use of the composition.

EXAMPLE A

A lubricating composition is prepared by blending a SAE 10W-30 mineral lubricating oil with approximately 10% by weight of a viscosity index improver and 7.5% by weight of a dispersant.

EXAMPLE B

A lubricating composition is prepared by blending a SAE 10W-30 mineral lubricating oil with approximately 10% by weight of a viscosity index improver, 7.5% by weight of a dispersant and 0.1% by weight of the acylated-nitrogen composition obtained by the process set forth in Example 6.

EXAMPLE C

A lubricating composition is prepared by preparing a blend of SAE 10W-30 mineral lubricating oil with approximately 10% by weight of a viscosity index improver, 7.5% by weight of a dispersant and 0.1% by weight of the oil soluble acylated-nitrogen composition obtained by the process set forth in Example 5.

EXAMPLE D

A lubricating composition is prepared by preparing a blend of SAE 10W-30 mineral lubricating oil with approximately 10% by weight of a viscosity index improver, 7.5% by weight of a dispersant and 0.1% by weight of the oil soluble acylated-nitrogen composition obtained by the process of Example 4.

The dispersant used in each of the above lubricating compositions (Examples A, B, C and D) comprises (1) approximately 65% by weight of a product obtained by reacting polyisobutenyl succinic anhydride with a polyethylene polyamine in the ratio of approximately 2.0 equivalents of said polyethylene polyamine per equivalent of said succinic anhydride; (2) approximately 16% by weight of a calcium phenate obtained by reacting calcium oxide in an aqueous medium with a phenol; (3) approximately 7% by weight of a calcium sulfonate; (4) approximately 9% by weight of a zinc dialkyl phosphorodithioate, and (5) approximately 3.0% by weight of mineral oil.

The effectiveness of the acylated-nitrogen compositions of this invention in a lubricating composition is illustrated by the data set forth in Table I.

TABLE I

| Lubricant | EMULSION TEST Days | | | | | |
|---|---|---|---|---|---|---|
| | 1 | 2 | 3 | 4 | 5 | 6 |
| EXAMPLE A | 5.0 | 4.0 | — | — | — | — |
| EXAMPLE B | 8.0 | 7.0 | 5.5 | 4.5 | 4.5 | — |
| EXAMPLE C | 8.5 | 6.5 | 6.5 | 5.5 | 5.0 | 5.0 |
| EXAMPLE D | 7.5 | 6.5 | 6.0 | 6.5 | 6.5 | 6.5 |

The demulsifying characteristic of the acylated-nitrogen compositions of this invention is illustrated by the Falcon engine test results presented in the Table. This test utilizes a Ford Falcon 6-cylinder engine operating on a cycling procedure consisting of 45 minutes at idle 500 RPM, no load, followed by 120 minutes at 2500 RPM, 31 BHP. The engine is modified by providing for water cooling of the rocker-arm cover in order to maintain a cover temperature of about 105°–115° F. During the cycle, the blow-by is passed through a condenser and the condensate is returned to the crankcase. The cycle is repeated 5 times in succession each day (for 13¾ hours of the engine operation) and then the engine is shut down for the remainder of the day (for 10¼ hours). The test is run on a consecutive day-to-day basis. The daily test evaluation consists of rating the rocker-arm cover for emulsion deposits on a numerical scale of 1 to 10, where 10 represents maximum cleanliness, i.e., freedom from aqueous emulsion deposits. The rocker-arm cover is removed and inspected after each 13¾ hours of operation and the cover then immediately replaced.

In addition to the acylated-nitrogen compositions of this invention, it is obvious that other known additives may be used in the fuel or lubricant. These additives include, for example, detergents of the ash-containing type, dispersants of the ashless type, viscosity index improving agents, pour-point depressing agents, anti-foam agents, extreme pressure agents, rust-inhibiting agents, oxidation and corrosion inhibiting agents, and various mixtures of these materials in various proportions. More particularly, the ash-containing detergents may be illustrated by the presently available oil soluble neutral and basic salts of the alkali or alkaline earth metals of the sulfonic acids, carboxylic acids, or the organic phosphorus acids. These materials may be prepared, for example, by the reaction of an olefin polymer, e.g. polyisobutene, having a molecular weight of about 2000 with a phosphorizing agent including, for example, phosphorus trichloride, phosphorus heptasulfide, phosphorus pentasulfide, phosphorus trichloride and sulfur, white phosphorus, and a sulfur halide or phosphorothioic chloride. The most commonly used salts of these acids, however, are the salts of sodium, potassium, lithium, calcium, magnesium, strontium, barium and various mixtures thereof.

The term "basic salt" as used herein is intended to include the metal salts where the metal is present in stoichiometrically larger amounts than the organic acid radical. The commonly employed methods for preparing the basic salts comprises heating a mineral oil solution of the acid with a stoichiometric excess of a metal neutralizing agent, e.g. a metal oxide, hydroxide, carbonate, bicarbonate, sulfide, etc., at temperatures above about 50° C. In addition, various promoters may be used in the neutralizing process to aid in the incorporation of the large excess of metal. These promoters are presently known and include such compounds as the phenolic substances, e.g. phenol, naphthol, alkylphenol, thiophenol, sulfurized alkylphenol and the various condensation products of formaldehyde with a phenolic substance, e.g. alcohols such as methanol, 2-propanol, octyl alcohol, cellosolve carbitol, ethylene, glycol, stearyl alcohol, and cyclohexyl alcohol; amines such as aniline, phenylenediamine, phenothiazine, phenyl-beta-naphthylamine, and dodecyl amine, etc. A particularly effective process for preparing the basic salts comprises mixing the acid with an excess of the basic alkaline earth metal in the presence of the phenolic promoter and a small amount of water and carbonating the mixture at an elevated temperature, e.g., 60° C. to about 200° C.

Extreme pressure agents, corrosion-inhibiting and oxidation-inhibiting agents are exemplified by chlorinated aliphatic hydrocarbons such as chlorinated wax; organic sulfides and polysulfides such as benzyl disulfide, bis(chlorobenzyl) disulfide, dibutyl tetrasulfide, sulfurized sperm oil, sulfurized methyl ester of oleic acid, sulfurized alkylphenol, sulfurized dipentene, and sulfurized terpene, phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl substituted phenyl phosphite; metal thiocarbamates such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptyl phenyl)-phosphorodithioate, cadmium dinonylphosphorodithioate, and zinc salt of a phosphorodithioic acid produced by the reaction of phosphorus pentasulfide with an equimolar mixture of isopropyl alcohol and n-hexyl alcohol.

The fuel or lubricating compositions may contain also metal detergent additives in amounts usually within the range of about 0.001% to about 15% by weight. In some applications, e.g., in lubricating marine diesel engines, the lubricating compositions may contain as much as 30% of a detergent additive. The compositions, e.g., lubricants or fuels, etc., may contain also extreme pressure agents, viscosity index improving agents, pour point depressing agents, etc., each in amounts within the range of from about 0.001 to 15% and preferably in amounts of 0.1% to about 10%. One or more of the above-mentioned additives may be used either alone or in combination in the compositions, e.g., fuels or lubricating oils, etc., with about 0.001% to 20% by weight and preferably 0.1% to 10% by weight of the acylated-nitrogen compositions of this invention.

The lubricants, i.e., the oleaginous materials include the animal oils and vegetable oils, e.g., castor oil, lard oil, etc., as well as solvent-refined or acid-refined mineral lubricating oils of the paraffinic, naphthenic, or mixed paraffinic-naphthenic types. Oils of lubricating viscosity derived from coal or shale are also useful base oils. The synthetic lubricating oils include the hydrocarbon oils and halo-substituted hydrocarbon oils such as polymerized and interpolymerized olefins (e.g., polybutylenes, propylene-isobutylene copolymers, chlorinated polybutylenes, etc.); alkyl benzenes (e.g., dodecylbenzene, tetradecylbenzene, dinonylbenzene, di-(2-ethylhexyl) benzene, etc.); polyphenyls (e.g., bi-phenyls, terphenyls, etc.); and the like. The alkylene oxide polymers and interpolymers and derivatives thereof where the terminal hydroxyl groups have been modified by esterification, etherification, etc., comprise another class of known synthetic lubricating oils. These are exemplified by the oils prepared by polymerization of ethylene oxide, propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500 to 1000, diethyl ether of polypropylene glycol having a molecular weight of 1000 to 1500, etc.) or mono- and polycarboxylic esters thereof, the acetic acid esters, mixed $C_3$–$C_8$ fatty acid esters, or the $C_{13}$ Oxo acid diester of tetraethylene glycol.

Another class of synthetic lubricating oils comprises the esters of dicarboxylic acids (e.g., phthalic acid, succinic acid, maleic acid, azelaic acid, suberic acid, sebacic acid, fumaric acid, adipic acid, linoleic acid dimer, etc.) with a variety of alcohols (e.g., butyl alcohol, hexyl alcohol, dodecyl alcohol, 2-ethylhexyl alcohol, pentaerythritol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicoxyl sebacate, the 2-ethylhexyl diester of linoleic acid dimer, the complex ester formed by reacting one mole of sebacic acid with two moles of 2-ethyl-hexanoic acid, and the like.

Silicone-based oils such as the polyalkyl-, polyaryl-, polyalkoxy-, or polyaryloxy-siloxane oils and silicate oils comprise another useful class of synthetic lubricants (e.g., tetraethyl-silicate, tetraisopropylsilicate, tetra-(2-ethylhexyl)-silicate, tetra-(4-methyl-2-tetraethyl)-silicate, tetra-(p-tert-butylphenyl)-silicate, hexyl-(4-methyl-2-pentoxy)-disiloxane, poly(methyl)siloxanes, poly(methylphenyl)-siloxanes, etc.). Other synthetic lubricants include the liquid esters of phosphorus-containing acids (e.g., tricresyl phosphate, trioctyl phosphate, diethyl ester of decane phosphonic acid, etc.), polymeric tetrahydrofurans, and the like.

While this invention is described with a number of specific embodiments, it is obvious that there are other variations and modifications which can be made without departing from the spirit and scope of the invention as particularly set forth in the appended claims.

What is claimed is:

1. An oil soluble acylated-nitrogen composition, having demulsifying characteristics, obtained by the acylation of (I) at least one polyoxyalkylene polyamine, having an average molecular weight of at least about 200, and selected from the group consisting of those corresponding to the formula, $H_2N$—Alkylene—$(O$—Alkylene$)_m$—$NH_2$, and R$+$Alkylene—$(O$—Alkylene$)_n$—$NH_2]_{3-6}$, wherein m has a value of about 3 to about 70, n has a value of about 1 to about 40 with the proviso that the sum of all of the n's is from about 3 to about 70 and R is a polyvalent saturated hydrocarbon radical of up to 10 carbon atoms and has a valence of 3 to 6; with (II) at least one carboxylic acid acylating agent selected from the group consisting of carboxylic acids, anhydrides, lower alkyl esters derived from monohydric lower aliphatic alcohols, and halides, and having at least 8 aliphatic carbon atoms; wherein the total amount of (I) and (II) used in the acylation is such that there is at least 0.001 equivalent of (I) per equivalent of (II).

2. The acylated-nitrogen composition of claim 1, wherein the amount of polyoxyalkylene polyamine (I) used is an amount ranging from about 0.001 to about 4.0 equivalents per equivalent of acylating agent (II).

3. The acylated-nitrogen composition of claim 1, wherein the acylating agent (II) is a substantially saturated hydrocarbon-substituted carboxylic acid acylating agent having at least about fifty aliphatic carbon atoms per carboxylic group.

4. The acylated-nitrogen composition of claim 3, wherein the acylating agent (II) is a substituted succinic acid or anhydride.

5. The acylated-nitrogen composition of claim 4, wherein the substituents are derived from the group consisting of ethylene-propylene copolymer, polypropylene, polyisobutylene, chlorinated ethylene-propylene copolymer, chlorinated polypropylene, and chlorinated polyisobutylene.

6. The acylated-nitrogen composition of claim 1, wherein the polyoxyalkylene polyamine (I) has an average molecular weight in the range of from about 200 to about 4000.

7. The acylated-nitrogen composition of claim 6, wherein the polyoxyalkylene polyamine (I) is a diamine.

8. The acylated-nitrogen composition of claim 6, wherein the polyoxyalkylene polyamine (I) is a triamine.

9. An oil soluble acylated-nitrogen composition, having demulsifying characteristics, obtained by the acylation of (I) at least one polyoxyalkylene polyamine having an average molecular weight in the range of from about 200 to about 4000, and selected from the group consisting of those corresponding to the formula, $H_2N$—Alkylene—$(O$—Alkylene$)_m$—$NH_2$, and R$+$Alkylene—$(O$—Alkylene$)_n$—$NH_2]_{3-6}$, wherein m has a value of about 3 to about 70, n has a value of about 1 to about 40 with the proviso that the sum of all of the n's is from about 3 to about 70 and R is a polyvalent saturated hydrocarbon radical of up to 10 carbon atoms and has a valence of three to six; with (II) at least one carboxylic acid acylating agent having a substantially saturated aliphatic hydrocarbon substituent with an average molecular weight of from about 400 to about 10,000, and the acylating agent is selected from the group consisting of carboxylic acids, anhydrides, lower alkyl esters derived from monohydric lower aliphatic alcohols, and halides; wherein the total amount of (I) and (II) used in the acylation is such that there is from about 0.001 to about 4.0 equivalents of (I) per equivalent of (II).

10. The acylated-nitrogen composition of claim 9, wherein the acylating agent is a monocarboxylic acid.

11. The acylated-nitrogen composition of claim 10, wherein the acylating agent is a substituted acrylic acid.

12. The acylated-nitrogen composition of claim 9, wherein the acylating agent is a substituted succinic acid or the anhydride thereof.

13. The acylated-nitrogen composition of claim 12, wherein the substituted succinic acid or anhydride has substituents selected from the group consisting of ethylene-propylene copolymer, polypropylene, polyisobutylene, chlorinated ethylenepropylene copolymer, chlorinated polypropylene and chlorinated polyisobutylene.

14. An oil soluble acylated-nitrogen composition, having demulsifying characteristics, obtained by the acylation of (I) at least one polyoxyalkylene polyamine selected from the group consisting of those corresponding to the formula, $H_2N$—Alkylene—$(O$—Alkylene$)_m NH_2$, and R$+$Alkylene—$(O$—Alkylene$)_n$—$NH_2]_{3-6}$, wherein m has a value of about 10 to about 35, n has a value of about 1 to about 40 with the proviso that the sum of all of the n's is from about 6 to about 35 and R is a polyvalent saturated hydrocarbon radical of up to 10 carbon atoms and has a valence of three to six; with (II) at least one carboxylic acid acylating agent, having at least eight aliphatic carbon atoms and selected from the group consisting of carboxylic acids, anhydrides, lower alkyl esters derived from monohydric lower aliphatic alcohols and halides; wherein the total amount of (I) and (II) used in the acylation is such that there is at least about 0.001 equivalent of (I) per equivalent of (II).

15. The acylated-nitrogen composition of claim 14, wherein the polyoxyalkylene polyamine (I) corresponds to the formula, $H_2N$—Alkylene—$(O$—Alkylene$)_m$—$NH_2$, and the acylating agent (II) is a substituted dicarboxylic acid or anhydride in which the substituents are derived from 1-olefin polymers or halogenated 1-olefin polymers, and have an average molecular weight in the range of from about 700 to 5000.

16. The acylated-nitrogen composition of claim 14 wherein the polyoxyalkylene polyamine (I) corresponds to the formula R$+$Alkylene—$(O$—Alkylene$)_n$—$NH_2]_{3-6}$, and the acylating agent (II) is a substituted dicarboxylic acid or anhydride in which the substituents are derived from 1-olefin polymers or halogenated 1-olefin polymers and have an average molecular weight in the range of from about 700 to about 5000.

17. An oil soluble acylated-nitrogen composition, having demulsifying characteristics, obtained by the acylation at a reaction temperature in the range of 25° C. to 300° C. of (I) at least one polyoxyalkylene polyamine having an average molecular weight in the range of from about 200 to about 4000 and is selected from the group consisting of those corresponding to the formula, $H_2N$—Alkylene—$(O$—Alkylene$)_m$—$NH_2$, and R$+$Alkylene—$(O$—Alkylene$)_n$—$NH_2]_{3-6}$ wherein m has a value of about 3 to about 70, and n has a value of from about 1 to about 40 with the proviso that the sum of all of the n's is from about 3 to about 70, and R is a polyvalent saturated hydrocarbon radical of up to 10 carbon atoms and has a valence of 3 to 6; with (II) at least one substituted succinic acid acylating agent selected from the group consisting of the acid or the anhydride, and having substituents derived from the group consisting of ethylene-propylene copolymer, polypropylene, polyisobutylene, chlorinated ethylene-propylene copolymer, chlorinated polypropylene and chlorinated polyisobutylene and having an average molecular weight in the range of from about 700 to about 5000; wherein the total amount of (I) and (II) used in the acylation is such that there is from about 0.1 to about 2.0 equivalents of (I) per equivalent of (II).

* * * * *